(12) United States Patent
Zeng et al.

(10) Patent No.: US 11,120,982 B2
(45) Date of Patent: Sep. 14, 2021

(54) MONITORING METHOD BASED ON THE DETECTION OF HUMAN INGESTED SUBSTANCE

(71) Applicant: XIAMEN LISI TECH SERVICE CO., LTD., Xiamen (CN)

(72) Inventors: Zhiyin Zeng, Xiamen (CN); Kongtao Zhu, Xiamen (CN); Hui Wu, Xiamen (CN); Jiansheng Zeng, Xiamen (CN); Henglin Luo, Xiamen (CN); Mingyi Hong, Xiamen (CN)

(73) Assignee: XIAMEN LISI TECH SERVICE CO., LTD., Xiamen (CN)

( * ) Notice: Subject to any disclaimer, the term of this patent is extended or adjusted under 35 U.S.C. 154(b) by 0 days.

(21) Appl. No.: 16/820,676

(22) Filed: Mar. 16, 2020

(65) Prior Publication Data
US 2021/0183636 A1 Jun. 17, 2021

(51) Int. Cl.
*H01J 49/16* (2006.01)
*H01J 49/00* (2006.01)

(52) U.S. Cl.
CPC ........ *H01J 49/164* (2013.01); *H01J 49/0027* (2013.01)

(58) Field of Classification Search
CPC .......................... H01J 49/164; H01J 49/0027
See application file for complete search history.

(56) References Cited

U.S. PATENT DOCUMENTS

2015/0031048 A1* 1/2015 Van Eyk ............. H01J 49/0027
435/7.4

* cited by examiner

*Primary Examiner* — Nicole M Ippolito
*Assistant Examiner* — Hanway Chang

(57) ABSTRACT

A monitoring method based on the detection of human ingested substances, comprises: acquiring the mass spectrum in the terminal of each matrix assisted laser ionization analysis time-of-flight mass spectrometer, and storing each mass spectrum and its corresponding identity information, sampling time and residence information when sampling in the database; obtaining the mass spectrum characteristic ion peaks of known substances and/or unknown substances in each mass spectrum; and counting the frequency of the mass spectrum characteristic ion peak of the known substance and/or the unknown substance, and early warning of the mass spectrum characteristic ion peak whose frequency is greater than the first threshold.

4 Claims, 6 Drawing Sheets

S1, obtaining hair samples or nail samples, wherein the hair samples are obtained by cutting the hair close to the scalp, and the nail samples are obtained by scraping a continuous layer from the root of the nail to the front edge of the nail S5, sampling the hair samples or nail samples per unit length, and judging whether the target ingested substance and its metabolites are present in each sample S6, counting times of detected target ingested substance and its metabolites as the ingestion times.

FIG. 3

MONITORING METHOD BASED ON THE DETECTION OF HUMAN INGESTED SUBSTANCE

CROSS REFERENCE TO RELATED APPLICATIONS

This application claims all benefits accruing under 35 U.S.C. § 119 from China Patent Application No. 201911302376.7, filed on Dec. 17, 2019, in the State Intellectual Property Office of China, the disclosure of which is incorporated herein by reference.

TECHNICAL FIELD

The disclosure related to a monitoring method based on the detection of human ingested substance.

BACKGROUND

At present, the number of cases involving drugs, stimulants or psychotropic substances is on the rise, so the in vivo analysis of drugs, stimulants or psychotropic substances and their metabolites has attracted more and more attention. In the prior art, drugs, stimulants or psychotropic substances can be detected by biological test materials to obtain corresponding detection data. However, there is no effective method to use the detection data for further big data monitoring or early warning analysis in the prior art.

SUMMARY OF THE DISCLOSURE

The disclosure provides a monitoring method based on the detection of human ingested substances, which can effectively solve the above problems.

The disclosure is realized as follows:

A monitoring method based on the detection of human ingested substance, comprising the following steps:

S1, acquiring the mass spectrum in the terminal of each matrix assisted laser ionization analysis time-of-flight mass spectrometer, and storing each mass spectrum and its corresponding identity information, sampling time and residence information when sampling in the database;

S2, obtaining the mass spectrum characteristic ion peaks of known substances and/or unknown substances in each mass spectrum;

S3, counting the frequency of the mass spectrum characteristic ion peak of the known substance and/or the unknown substance, and early warning of the mass spectrum characteristic ion peak whose frequency is greater than the first threshold.

The beneficial effect of the disclosure is that the mass spectrum and its corresponding identity information and other big data are stored in the database, and the frequency of the mass spectrum characteristic ion peak of the known and/or unknown substances is counted, so that the mass spectrum characteristic ion peak whose frequency is greater than the first threshold can be early warned, and then the big data monitoring of drug abuse, poisoning event, or pollution event can be realized.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

FIG. 3 is a schematic diagram of the detection principle in the matrix assisted laser ionization analysis time-of-flight mass spectrometer according to an embodiment of the disclosure.

DETAILED DESCRIPTION

The disclosure is illustrated by way of example and not by way of limitation in the figures of the accompanying drawings in which like references indicate similar elements. It should be noted that references to "an" or "a" embodiment in this disclosure are not necessarily to the same embodiment, and such references mean "at least one."

Figure 1:
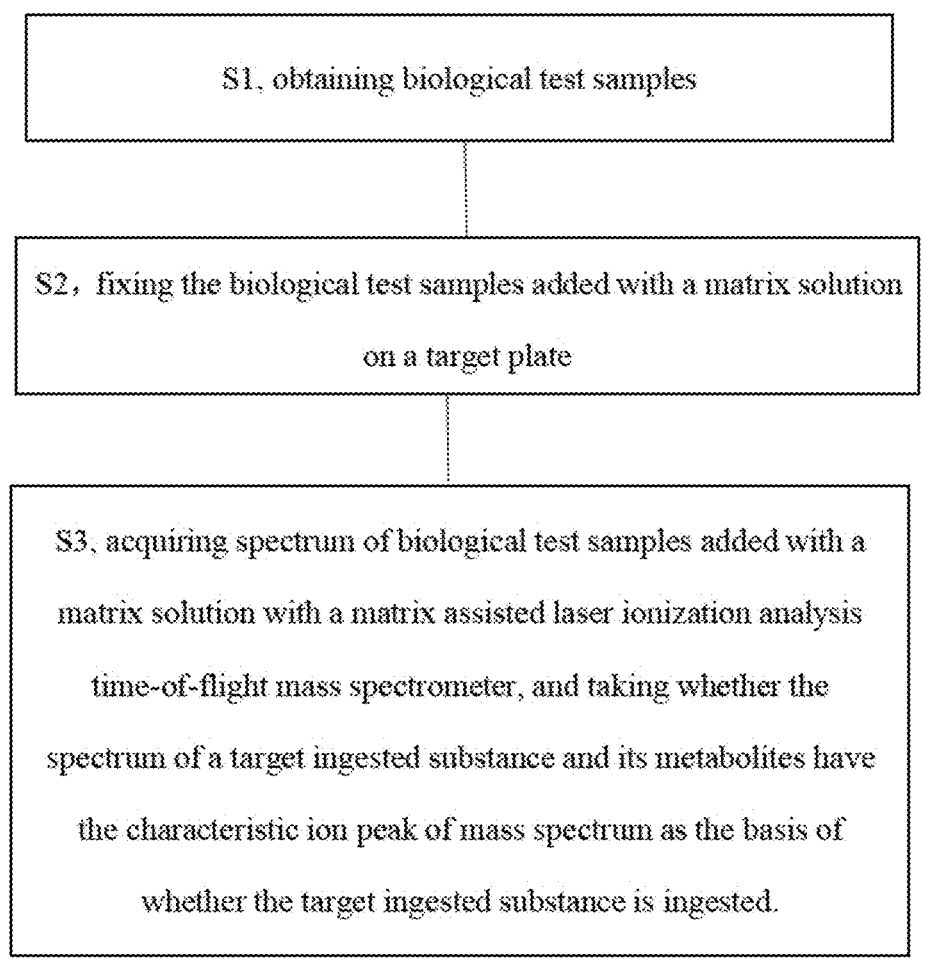
FIG. 1 is a flow chart of a monitoring method based on the detection of human ingested substances according to an embodiment of the disclosure.

Referring to FIG. 1, the embodiment of the disclosure provides a monitoring method based on the detection of human ingested substances, which comprises the following steps:

S1, acquiring the mass spectrum in the terminal of each matrix assisted laser ionization analysis time-of-flight mass spectrometer, and storing each mass spectrum and its corresponding identity information, sampling time and residence information when sampling in the database;

S2, obtaining the mass spectrum characteristic ion peaks of known and/or unknown substances in each mass spectrum;

S3, counting the frequency of the mass spectrum characteristic ion peak of the known substance and/or the unknown substance, and early warning of the mass spectrum characteristic ion peak whose frequency is greater than the first threshold.

Figure 2:
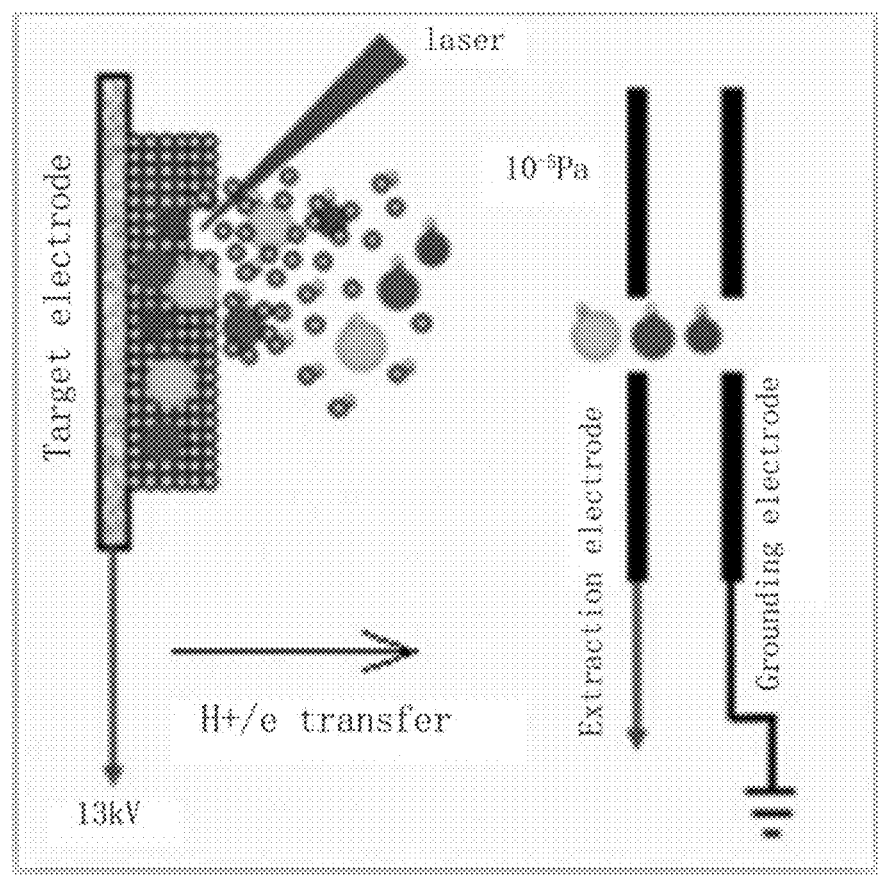
FIG. 2 is a flow chart of obtaining a mass spectrum diagram according to an embodiment of the present disclosure.

Referring to FIG. 2, in step S1, the identity information is not limited to name, gender, age, nationality, etc. The residence information refers to the place where the sampled person has been living continuously for a certain period of time.

The step of acquiring the mass spectrum in the terminal of each matrix assisted laser ionization analysis time-of-flight mass spectrometer comprises:

S11, obtaining biological samples;

S12, fixing the biological samples added with matrix solution on a target plate;

S13, acquiring spectrum of biological samples added with matrix solution with matrix assisted laser ionization analysis time-of-flight mass spectrometer.

In step S11, the biological samples are preferably hair samples or nail samples, wherein the hair samples are obtained by cutting the hair close to the skin, and the nail samples are obtained by scraping a continuous layer from the root of the nail to the front edge of the nail. The biological samples can also be blood, saliva or other excreta, etc. In this embodiment, the hair at the occipital part is selected. There is no limit to the number of hair samples and nail samples, preferably 2-3.

In step S11, after the hair samples or nail samples are obtained, further comprising:

S11.1 washing the hair samples or the nail samples to remove contaminants.

In step S12, the step of fixing the hair samples or nail samples added with matrix solution on a target plate comprises:

S12.1, fixing the hair samples or nail samples on a target plate;

S12.2, adding the matrix solution to the hair samples or the nail samples and volatilizing the solvent.

As a further improvement, the matrix molecules must have strong absorption at the laser wavelength. The matrix in the matrix solution can be one or more of α-cyano-4-hydroxycinnamic acid, 3,5-dimethoxy-4-hydroxycinnamic acid, trihydroxyacetophenone, 3-hydroxypyridylic acid, α-cyano-4-hydroxycinnamic acid, trihydroxyacetophenone, trans-3-indoleacrylic acid, desanthrol and 2,5-dihydroxybenzoic acid. The matrix solution can be formed by dissolving the matrix in a solvent.

As a further improvement, the matrix solution can further comprise an internal standard. The internal standard can be methoxyphenamine, etc.

Referring to FIG. 3, in step S13, the step of acquiring spectrum of hair or nail samples added with matrix solution with matrix assisted laser ionization analysis time-of-flight mass spectrometer comprises:

S13.1, preliminarily acquiring the spectrum of the hair samples or nail samples added with matrix solution with matrix assisted laser ionization analysis time-of-flight mass spectrometer;

The unit length can be selected according to the growth rate of human hair every day. Generally speaking, human hair varies from person to person, with a daily growth rate of about 0.2-0.4 mm. Therefore, preferably, the unit length is also 0.2-0.4 mm.

When the matrix solution further comprises an internal standard, after step s13.1, it may further comprise:

S13.2, judging whether the internal standard is detected in the mass spectrum, yes, the result is reliable; no, the result is unreliable, then go to step S31 to acquiring spectrum again.

It can be understood that if the internal standard is detected in the samples, the target ingested substance and its metabolite components are not detected, the negative result is reliable, and the ingestion times by the suspect is zero. If no internal standard is detected in the sample, the negative result is unreliable, and go to step S31 to collect spectrum again.

Generally speaking, the mass nucleus ratio of characteristic ion peaks of drugs, stimulants or abused drugs is generally below 1000. Therefore, all known types of drugs, stimulants or abused drugs can be obtained by scanning the characteristic ion peaks of drugs, stimulants or abused drugs within a certain range. Therefore, as a further improvement, the step of acquiring spectrum comprises:

S33, scanning ions with charge mass ratio of 0 to 2000 to form a mass spectrum.

In addition, the parameters of the matrix assisted laser ionization analysis time-of-flight mass spectrometer also have a great impact on the detection results. Preferably, the parameters of the matrix assisted laser ionization analysis time-of-flight mass spectrometer are: laser wavelength: 308, 337 nm or 405 nm, etc.; laser power: 0.5 to 5 uj; target high voltage: 10000 to 15000V; pulse high voltage: 1000 to 2000V; detector high voltage: 1500 to 2000V; lens high voltage: 500 to 2000V. In this embodiment, the parameters of the matrix assisted laser ionization analysis time-of-flight mass spectrometer are: laser wavelength: 337 nm; laser power: 1.9 uj; target high voltage: 13000V; pulse high voltage: 1500V; detector high voltage: 1600V; lens high voltage: 1000V.

Please refer to table 1 below. Table 1 shows the qualitative characteristic ion peaks of common drugs, metabolites and internal standards.

TABLE 1 shows the qualitative characteristic ion peaks of common drugs, metabolites and internal standards

| Drugs and metabolites | Characteristic ion peak/(M/z) |
|---|---|
| O6 monoacetylmorphine | 328; 211; 165 |
| Morphine | 286; 201; 165 |
| Codeine | 300; 199; 165 |
| MAMP | 150; 119; 91 |
| AMP | 136; 119; 91 |
| MDMA | 194; 163; 105 |
| MDA | 180; 163; 135 |
| MDEA | 208; 163; 105 |
| Ketamine | 238; 179; 125 |
| Norketamine | 224; 207; 125 |
| Cocaine | 304; 182; 150 |
| Benzoylecgonine | 290; 168; 105 |
| D9-Tetrahydrocannabinol | 315; 259; 193 |
| Cannabidiol | 315; 259; 193 |
| Cannabinol | 311; 293; 223 |
| Methoxyphenamine (internal standard) | 180; 149; 121 |

Figure 4:
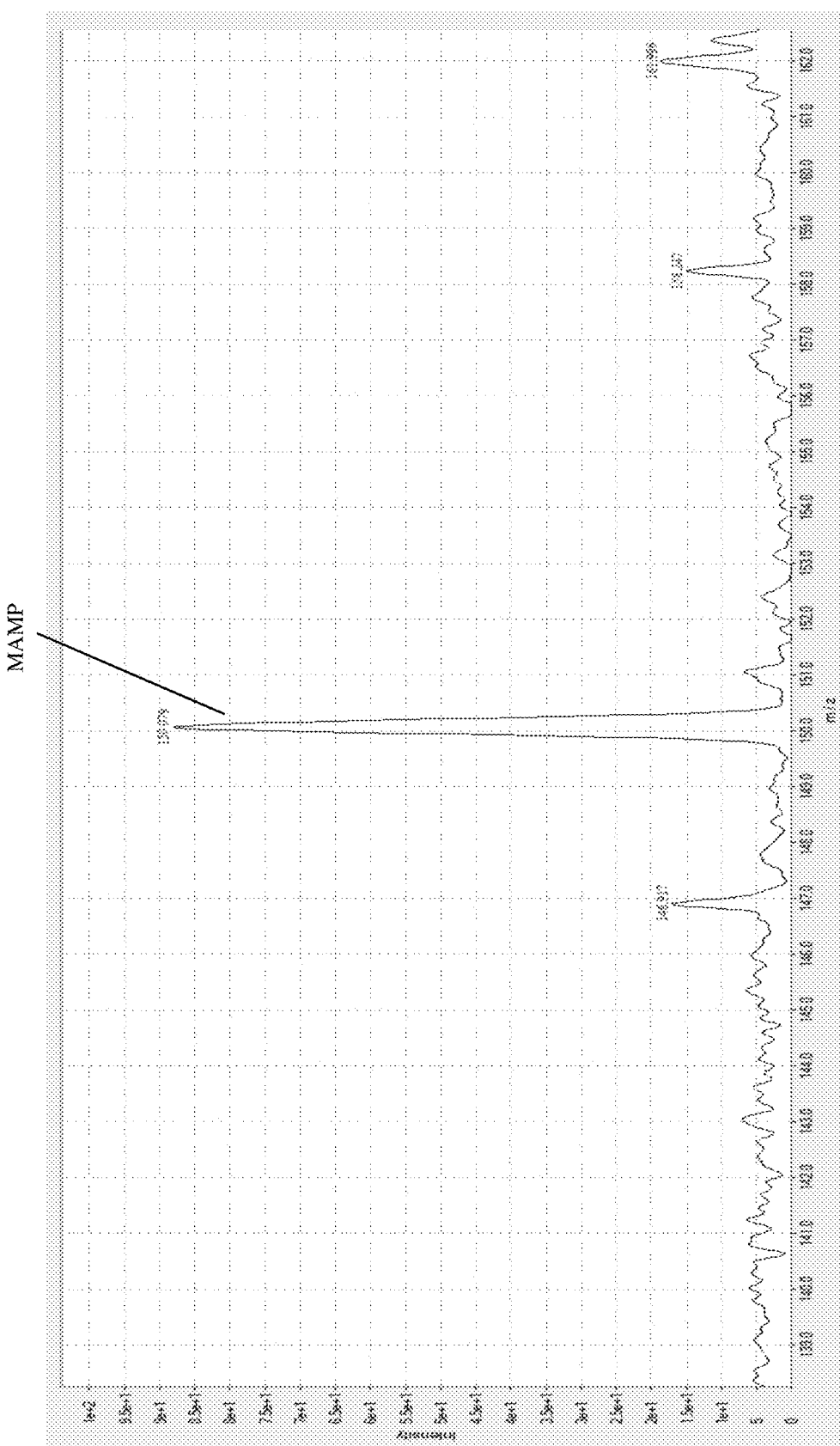
FIG. 4 is a mass spectrum of the hair detected according to embodiment 1.

Please refer to FIG. 4, which is the mass spectrum of the hair detected in embodiment 1, from which it can be seen that the hair has the mass spectrum characteristic ion peak of MAMP.

Figure 5:
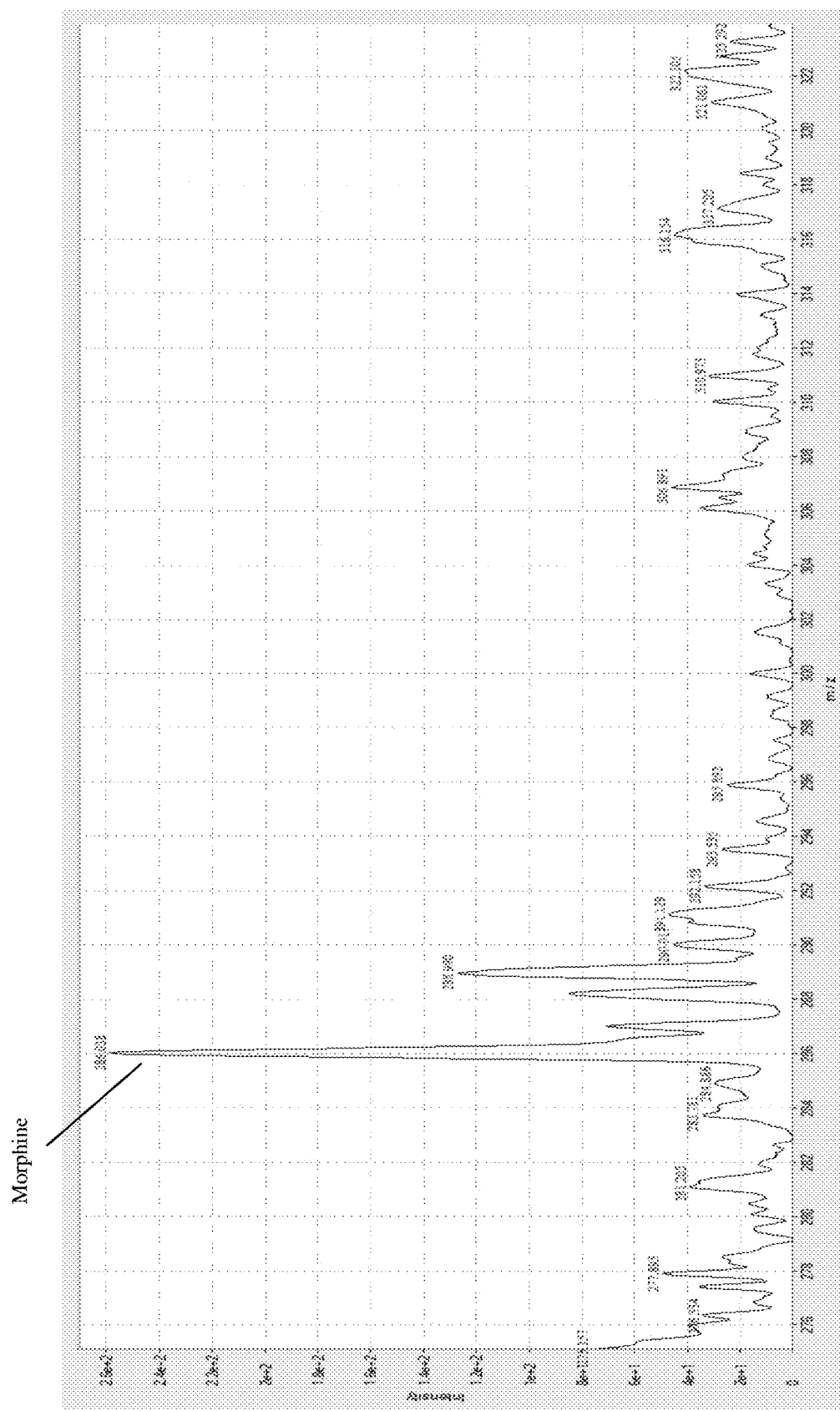
FIG. 5 is a mass spectrum of the hair detected according to embodiment 2.

Please refer to FIG. 5, which is the mass spectrum of the hair detected in embodiment 2. It can be seen that the hair has the mass spectrum characteristic ion peak of morphine.

Figure 6:
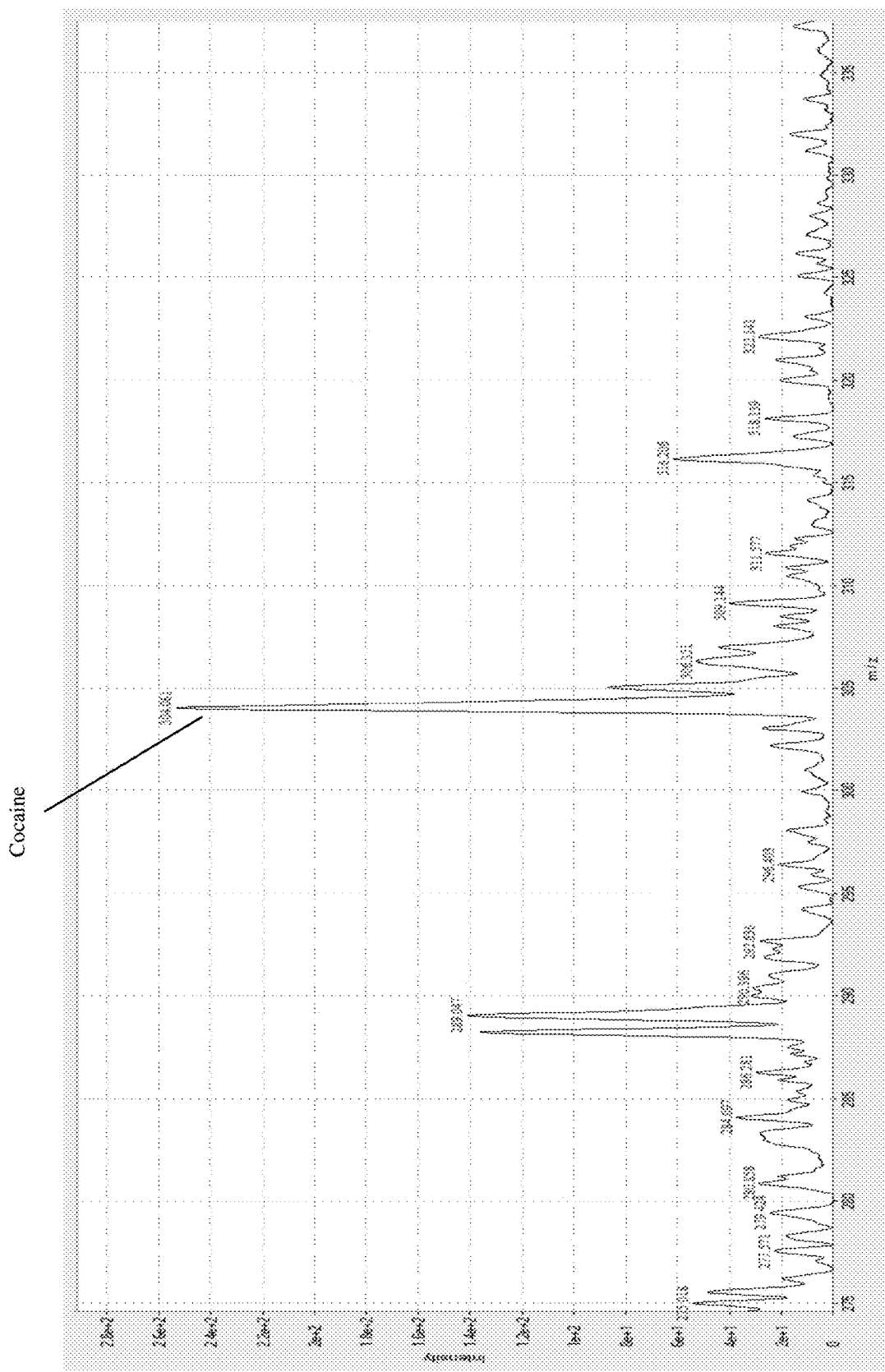
FIG. 6 is a mass spectrum of the hair detected according to embodiment 3.

Please refer to FIG. 6, which is the mass spectrum of the hair detected in embodiment 3, from which it can be seen that the hair has the mass spectrum characteristic ion peak of cocaine.

In step S3, by counting the frequency of the mass spectrum characteristic ion peak of the known substance (e.g. drug) and combining with the identity information, the probability of the occurrence of the drug ingestion event in a predetermined area can be early warned. In addition, by counting the frequency of the mass spectrum characteristic ion peak of the unknown substance (e.g. the unidentified new psychoactive drug) and combining with the identity information, the probability of the controlled substance ingestion event in the predetermined area can be early warned.

Specifically, after step S3, it can further comprise:

S4, obtaining the identity information of the mass spectrum corresponding to the mass spectrum characteristic ion peak whose frequency is greater than the first threshold;

S5, constructing a geographic location distribution model based on the sampling time and the residence information at the time of sampling.

The size of the geographic location distribution model is unlimited, which mainly depends on the source of data. It can be national, local or, of course, global.

In other embodiment, when a substance is comprised in a controlled substance, after step S3, it may further comprise:

S6, obtaining the mass spectrum with the same mass spectrum characteristic ion peak of the controlled substance in the database, so as to obtain the identity information corresponding to the mass spectrum for traceability.

The controlled substances can be drugs, stimulants, drug abuse, etc.

In other embodiment, when a substance is comprised in the pollution source, after step S3, it further comprises:

S7, obtaining the mass spectrum with the same mass spectrum characteristic ion peak as the pollution source in the database, so as to obtain the identity information corresponding to the mass spectrum for traceability.

For example: detection and traceability of pesticide residues.

The above-described embodiments are intended to illustrate rather than limit the disclosure. Variations may be made to the embodiments without departing from the spirit of the disclosure as claimed. The above-described embodiments illustrate the scope of the disclosure but do not restrict the scope of the disclosure.

What is claimed is:

1. A monitoring method based on the detection of human ingested substance, comprising:
    acquiring the mass spectrum in the terminal of each matrix assisted laser ionization analysis time-of-flight mass spectrometer, and storing each mass spectrum and its corresponding identity information, sampling time and residence information when sampling in the database;
    obtaining the mass spectrum characteristic ion peaks of known substances and/or unknown substances in each mass spectrum;
    counting the frequency of the mass spectrum characteristic ion peak of the known substance and/or the unknown substance, and early warning of the mass spectrum characteristic ion peak whose frequency is greater than the first threshold;
    obtaining the identity information of the mass spectrum corresponding to the mass spectrum characteristic ion peak whose frequency is greater than the first threshold; and
    constructing a geographic location distribution model based on the sampling time and the residence information at the time of sampling.

2. The method according to claim 1, wherein the step of acquiring the mass spectrum in the terminal of each matrix assisted laser ionization analysis time-of-flight mass spectrometer comprises:
    obtaining biological samples;
    fixing the biological samples added with a matrix solution on a target plate; and
    acquiring the mass spectrum of biological samples added with a matrix solution with a matrix assisted laser ionization analysis time-of-flight mass spectrometer.

3. The method according to claim 1, wherein when a substance is comprised in a controlled substance, after the step of counting the frequency of the mass spectrum characteristic ion peak of the known substance and/or the unknown substance, the method further comprises:
    obtaining the mass spectrum with the same mass spectrum characteristic ion peak of the controlled substance in the database, so as to obtain the identity information corresponding to the mass spectrum for traceability.

4. The method according to claim 1, wherein when a substance is comprised in a pollution source, after the step of counting the frequency of the mass spectrum characteristic ion peak of the known substance and/or the unknown substance, the method further comprises:
    obtaining the mass spectrum with the same mass spectrum characteristic ion peak as the pollution source in the database, so as to obtain the identity information corresponding to the mass spectrum for traceability.

\* \* \* \* \*